(12) United States Patent
Cummins et al.

(10) Patent No.: US 10,285,745 B2
(45) Date of Patent: May 14, 2019

(54) ORTHOPEDIC SCREWS

(71) Applicant: Zavation, LLC, Flowood, MS (US)

(72) Inventors: John Franklin Cummins, Kosciusko, MS (US); John Lawrence Walker, Madison, MS (US)

(73) Assignee: ZAVATION MEDICAL PRODUCTS LLC, Flowood, MO (US)

( * ) Notice: Subject to any disclaimer, the term of this patent is extended or adjusted under 35 U.S.C. 154(b) by 218 days.

(21) Appl. No.: 15/201,643

(22) Filed: Jul. 5, 2016

(65) Prior Publication Data

US 2018/0008329 A1   Jan. 11, 2018

(51) Int. Cl.
*F16B 25/10* (2006.01)
*A61B 17/70* (2006.01)
*A61B 17/86* (2006.01)

(52) U.S. Cl.
CPC ...... *A61B 17/8635* (2013.01); *A61B 17/7035* (2013.01); *F16B 25/103* (2013.01); *A61B 17/864* (2013.01)

(58) Field of Classification Search
CPC ............ A61B 17/7032; A61B 17/7035; A61B 17/8635; F16B 25/103; F16B 25/106
See application file for complete search history.

(56) References Cited

U.S. PATENT DOCUMENTS

| 5,098,435 | A | * | 3/1992 | Stednitz | A61B 17/1637 |
| | | | | | 411/387.5 |
| 7,731,738 | B2 | * | 6/2010 | Jackson | A61B 17/8635 |
| | | | | | 606/300 |
| 9,358,057 | B1 | * | 6/2016 | Whipple | A61B 17/7055 |
| 2003/0055426 | A1 | * | 3/2003 | Carbone | A61B 17/7034 |
| | | | | | 606/271 |
| 2006/0149263 | A1 | | 7/2006 | Newcomb et al. | |
| 2014/0277188 | A1 | | 9/2014 | Poulos | |
| 2016/0120583 | A1 | | 5/2016 | Bales | |

* cited by examiner

*Primary Examiner* — Nicholas W Woodall
(74) *Attorney, Agent, or Firm* — Tarolli, Sundheim, Covell & Tummino LLP

(57) ABSTRACT

Self-drilling, self-tapping and self-advancing orthopedic screws are provided. An orthopedic screw includes a relief cut at the tip of the screw that is timed to the distal-most thread at the end of the screw tip to create a wide and sharp cutting edge for the screw.

12 Claims, 3 Drawing Sheets

ORTHOPEDIC SCREWS

TECHNICAL FIELD

The present disclosure generally relates to self-drilling, self-tapping and self-advancing orthopedic screws.

BACKGROUND

A variety of fasteners are used in orthopedic surgical procedures to secure bone fragments, reattach ligaments or soft tissue to bones, or to stabilize bones in relative position to one another. For example, cervical plates are typically secured to vertebrae with bone screws to stabilize the cervical spine Likewise, occipital plates are typically secured to the back of the skull with bone screws for attaching spinal rods. Pedicle screws are inserted into the pedicle of a vertebral body and are commonly used along with rods and screws to immobilize a portion of the spinal column. In other applications, pedicle screws are inserted into a series of vertebrae and one or more metal rods are secured to the heads of the screws, typically using set screws or some other securing means.

Many orthopedic screw designs require multiple steps to insure proper implantation into bone. Typically, an entry point is made in the bone using a high speed drill bit to create a pilot hole. The pilot hole may then be probed with an instrument to detect any breaches in the bone wall. After the integrity of the bone wall is confirmed, the pilot hole is then tapped to create a track in the bone wall for the orthopedic screw to follow using a tap. Finally, the screw may be implanted into the prepared hole. Others procedures involve driving self-tapping screws into pre-drilled pilot holes. Still other procedures involve driving self-drilling screws directly into the bone without pre-drilling or pre-tapping.

Procedures which require multiple steps can create the potential for the patient to experience complications with each step. Additionally, the chances for a surgeon to make a mistake due to fatigue during long procedures involving multiple screws increases with the number of steps required for placement of each screw. Thus, there is a need for an improved orthopedic screw that reduces the number of steps required for implanting the screw into bone.

SUMMARY

The present disclosure relates to orthopedic screws. In an embodiment, an orthopedic screw is provided that comprises a main shaft extending along a central axis from a proximal end to a distal end. The main shaft comprises a plurality of threads between the proximal end and the distal end of the main shaft. The orthopedic screw also includes a tip that extends along the central axis from the distal end of the main shaft. The tip has a minor diameter and a major diameter. The tip comprises a tip shaft defining the minor diameter of the tip. The tip also includes a distal-most thread that has a leading edge and defines the major diameter of the tip. The distal-most thread also ends the tip. The tip further includes a relief cut having a leading end and a trailing end. The trailing end extends in a plane different than the leading edge of the distal-most thread. The leading end of the relief cut starts at the leading edge of the distal-most thread.

DETAILED DESCRIPTION

The present disclosure generally related to orthopedic screws. In particular, aspects of the present disclosure provide self-drilling and self-tapping orthopedic screws. Screws of the present disclosure can be used to simultaneously form a pilot hole in bone and form threads for securing the screw in bone as the screw is secured into bone. Such a screw does not require the separate step of forming a pilot hole in the bone and then tapping the bone for insertion of the screw into the bone.

The present disclosure refers to the term "substantially" with respect to certain geometric shapes. By "substantially" is meant that the shape of the element need not have the mathematically or geometrically exact described shape but can have a shape that is recognizable by one skilled in the art as generally or approximately having the described shape. As used herein with respect to a described element, the terms "a," "an," and "the" include at least one or more of the described element unless otherwise indicated. Further, the term "or" refers to "and/or" unless otherwise indicated. In addition, it will be understood that when an element is referred to as being "on," "attached" to, "connected" to, "coupled" to etc., another element, it can be directly on, attached to, connected to, coupled to, etc. the other element or intervening elements may also be present. In contrast, when an element is referred to as being, for example, "directly attached" to, "directly connected" to or "directly coupled" to another element, there are no intervening elements present. Further, as used herein the term "about" means +−50% of the recited value.

Figure 1:
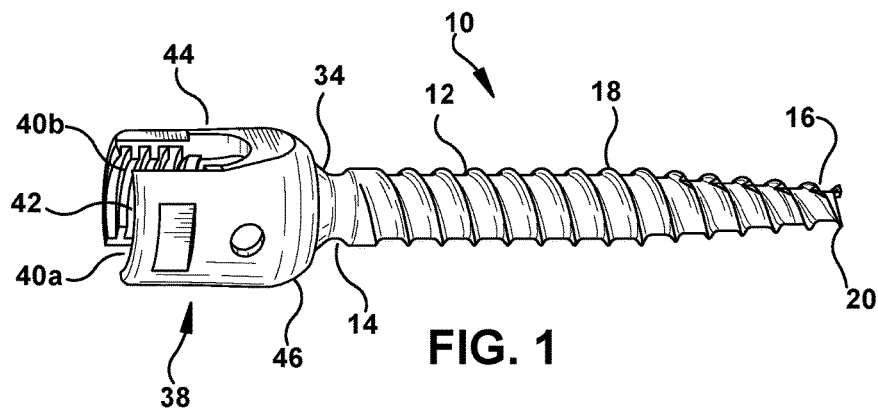
FIG. 1 is a perspective view of an orthopedic screw with a connector assembly attached to the head of the orthopedic screw according to an embodiment of the present disclosure.
Figure 2:
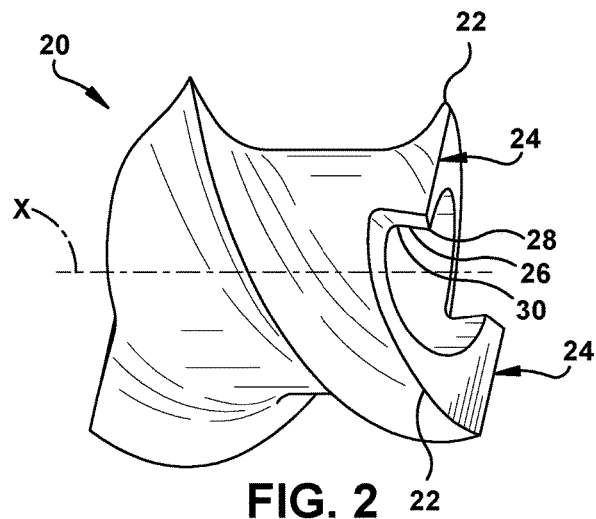
FIG. 2 is a perspective view of a screw tip of the orthopedic screw depicted in FIG. 1.
Figure 3:
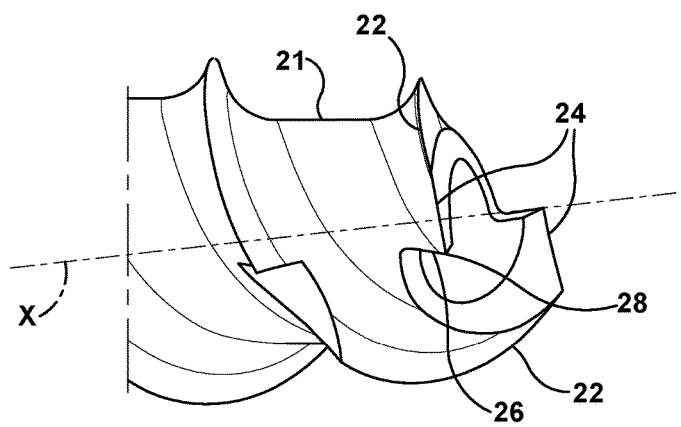
FIG. 3 is a perspective view of the screw tip depicted in FIG. 2 rotated 180 degrees.
Figure 8:
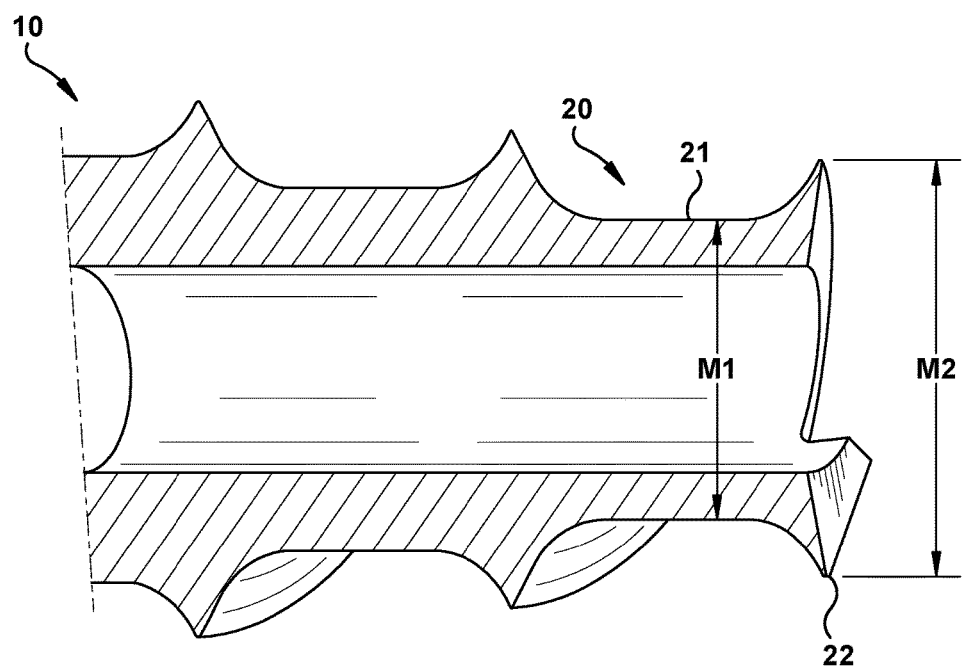
FIG. 8 is a partial cross-section of the orthopedic screw of FIG. 1 identifying the major and minor diameter of the screw tip according to an embodiment of the present disclosure.

Referring to FIG. 1, in an embodiment, an orthopedic screw 10 comprises a main shaft 12 extending along a central axis X from a proximal end 14 to a distal end 16. Shaft 12 comprises a plurality of threads 18 between proximal end 14 and distal end 16. Preferably, the plurality of threads extends the entire length of the main shaft between the proximal end and the distal end of the main shaft. Also, preferably the plurality of threads taper from the proximal end to the distal end so that as the pilot hole is being created, the plurality of threads bites into the sides of the pilot hole advancing the orthopedic screw deeper into the bone. Such a configuration provides the screw with self-advancing features to improve insertion of the orthopedic screw into bone. Orthopedic screw 10 further includes a tip 20 extending along central axis X from distal end 16 of shaft 12. Tip 20 has a minor diameter M1 and a major diameter M2 as illustrated in FIG. 8. Tip shaft 21 of tip 20 defines minor diameter M1 of tip 20. Tip 20 also includes a distal-most thread 22 have a leading edge 24 and defining major diameter M2 of tip 20. As can be seen from FIG. 8, major diameter M2 is the maximum diameter of tip 20 and minor diameter M1 is the minimum diameter of tip 20. Leading edge 24 of distal-most thread 22 is also referred to as the "cutting edge" of the orthopedic screw. The distal-most thread extends to the very end of tip 20 as illustrated in FIGS. 2 and 3. As such, the drilling diameter (e.g. the outer diameter of the pilot hole created when the orthopedic screw is inserted into bone) is the same diameter as the thread major diameter thereby improving the screw's ability to be advanced into bone.

Tip 20 further includes a relief cut 26 having a leading end 28 and a trailing end 30. Trailing end 30 extends in a plane different than leading edge 24 of distal-most thread 22. Leading end 28 of relief cut 26 starts at leading edge 24 of distal-most thread 22. Leading end 28 of relief cut 26 starts at leading edge 24 of distal-most thread 22 to create a wide cutting edge that can create a pilot hole for inserting the orthopedic screw into bone. The wide cutting edge allows the orthopedic screw to cut bone away as the orthopedic screw is rotated clockwise with minimal axial force and provides the screw with a self-drilling feature to improve initial insertion of the screw into bone. Further, because the distal-most thread extends to the very tip of the screw, the relief cut does not reduce the screw purchase.

Figure 6:
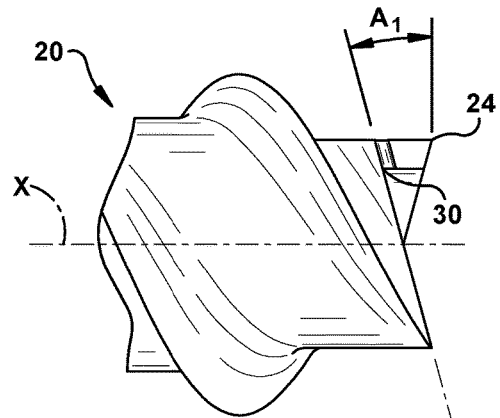
FIG. 6 is a perspective view of the screw tip of an orthopedic screw depicting an exemplary angular orientation of the trailing end of a relief cut of the orthopedic screw tip relative to the leading edge of the distal-most thread of the screw tip relative to the central axis of the screw's main shaft according to an embodiment of the present disclosure.

With reference to FIG. 6, in certain embodiments, the angular orientation A1 of trailing end 30 of relief cut 26 relative to leading edge 24 of distal-most thread 22 is between about 1 degree and about 30 degrees relative to central axis X. In certain embodiments, angular orientation A1 is about 15 degrees. Such angular orientation creates a sharp cutting edge to cut bone in a manner similar to a bone drill that is used to create a pilot hole. The aggressiveness of the cutting tip is significantly better than other self drilling screws in the art because the shallow angle of the cutting edge makes drilling into bone easier than other self drilling screws in the art. The shallow angle creates a knife edge that will cut bone easier than a steep angle, which would scrape the bone instead of cutting into bone.

Figure 7:
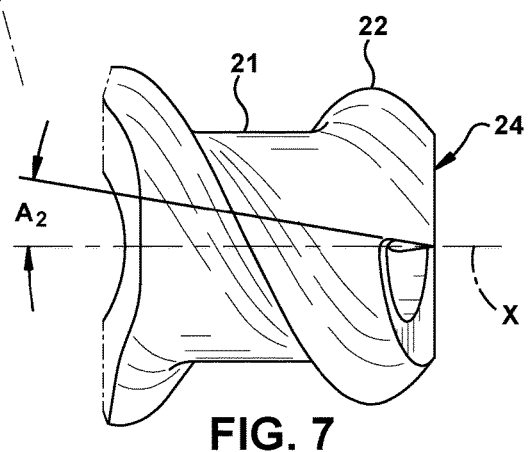
FIG. 7 is a perspective view of a screw tip of an orthopedic screw depicting an exemplary angular orientation of the leading end of a relief cut relative to the trailing end of the relief cut relative to the central axis of the screw's main shaft according to an embodiment of the present disclosure.

With reference to FIG. 7, in certain embodiments, the angular orientation A2 of leading end 28 of relief cut 26 relative to trailing end 30 of relief cut 26 is between about 0 degrees and about 17 degrees relative to central axis X. In certain embodiments, angular orientation A2 is about 8.5 degrees.

Figure 5:
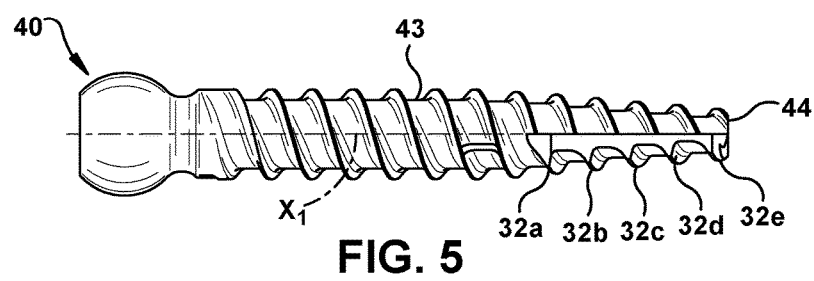
FIG. 5 is a side view of an orthopedic screw according to an embodiment of the present disclosure.

With reference to FIG. 5, in certain embodiments, an orthopedic screw 40 further includes blades 32 that extend radially outward from central axis X1 along which main shaft 42 and the tip shaft of orthopedic screw 40 extend. The blades are preferably located between the distal end of main shaft 43 and the tip 44 of screw 40. The blades can cut threads into the sides of the pilot hole as the screw is advanced into bone thus providing the screw with self-tapping features to improve insertion of the screw into bone.

Figure 4:
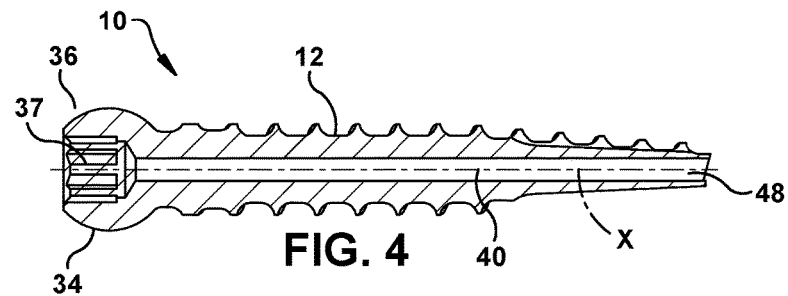
FIG. 4 is a cross-sectional view of an orthopedic screw according to an embodiment of the present disclosure.

An orthopedic screw as described herein can have a head from which the main shaft distally extends. The screw head can have any suitable orthopedic screw head configuration. Although the figures illustrate a polyaxial pedicle screw head that has a tulip-shaped configuration, the screw head can also be substantially round and define a socket for receiving a driver to install a pedicle screw or other types of orthopedic screws. With reference to FIGS. 1 and 4, in certain embodiments, orthopedic screw 10 includes a screw head 36 from which shaft 12 extends distally. Screw head 36 can include a ball-shaped spherical connector 34 and a driver receptacle 37 located along an upper end of spherical connector 34 configured to receive a driving tool to install orthopedic screw 10. The driver receptacle may be any shape, male or female, suitable for cooperation with a driving tool to rotate the orthopedic screw.

Referring back to FIG. 1, in certain embodiments, an orthopedic screw assembly is provided that includes the orthopedic screw as described above and further includes a connector assembly 38 defining a pair of opposing openings 40 and a channel 42 extending through the opposing openings 40. Channel 42 is configured to receive an orthopedic rod. Connector assembly 38 can have an upper threaded portion 44 configured to receive a set screw and a bottom socket portion 46 configured to cooperate with spherical connector 34.

Referring back to FIG. 4, in certain embodiments, the tip of the orthopedic screw is cannulated so as to define a hole 48 about the central axis X of main shaft 12. Various different orthopedic instrumentation can be inserted through hole 48 to aid in the insertion of the orthopedic screw.

The orthopedic screws of the present disclosure may be used in conjunction with bone cement that is injected into the bone structure into which the orthopedic screw is inserted so as to stabilize the bone structure and to increase the purchase of the orthopedic screw in bone structure having diminished or osteoporotic bone quality.

Although the present disclosure has been described primarily with respect to a pedicle screw, the orthopedic screw can be used for other orthopedic fixation procedures. For example, the orthopedic screw can be a cortical screw, a cancellous screw, a cannuled screw, a Herbert screw, and/or a malleolar screw.

Each of the disclosed aspects and embodiments of the present invention may be considered individually or in combination with other aspects, embodiments, and variations of the invention. Further, while certain features of embodiments of the present disclosure may be shown in only certain figures, such features can be incorporated into other embodiments shown in other figures while remaining within the scope of the present disclosure. In addition, unless otherwise specified, none of the steps of the methods of the present disclosure are confined to any particular order of performance. Modifications of the disclosed embodiments incorporating the spirit and substance of the present disclosure may occur to persons skilled in the art and such modifications are within the scope of the present disclosure. Furthermore, all references cited herein are incorporated by reference in their entirety.

What is claimed is:

1. An orthopedic screw comprising:
   a main shaft extending along a central axis from a proximal end to a distal end, the main shaft comprising a plurality of threads between the proximal end and the distal end; and
   a tip extending along the central axis from the distal end of the main shaft, the tip comprising:
   a distal-most thread have a leading edge and defining a major diameter of the tip, the distal-most thread defining the end of the tip and having a surface extending from the leading edge that is transverse to the central axis, the surface including a substantially planar portion adjacent to the leading edge; and a tip shaft proximal to the distal-most thread and defining a minor diameter of the tip; and a relief cut having a leading end and a trailing end, the trailing end extending in a plane different than the leading edge of the distal-most thread, the leading end of the relief cut starting at the leading edge of the distal-most thread.

2. The orthopedic screw of claim 1, wherein the angular orientation of the trailing end of the relief cut relative to the leading edge of the distal-most thread is between about 1 degree and about 30 degrees relative to the central axis of the main shaft.

3. The orthopedic screw of claim 2, wherein the angular orientation is about 15 degrees.

4. The orthopedic screw of claim 1, wherein the angular orientation of the leading end of the relief cut relative to the trailing end of the relief cut is between about 0 degrees and about 17 degrees relative to the central axis of the main shaft.

5. The orthopedic screw of claim 4, wherein the angular orientation is about 8.5 degrees.

6. The orthopedic screw of claim 1, further comprising blades that extend radially outward from the central axis of the main shaft.

7. The orthopedic screw of claim 6, wherein the blades are located between the tip and the distal end of the main shaft.

8. The orthopedic screw of claim 1, further comprising a screw head, the main shaft extending distally from the screw head.

9. The orthopedic screw of claim 8, wherein the screw head comprises a ball-shaped spherical connector, a driver receptacle located along an upper end of the spherical connector configured to receive a driving tool to install the orthopedic screw.

10. An orthopedic screw assembly comprising the orthopedic screw of claim 9 and further comprising a connector assembly defining a pair of opposing openings and a channel extending through the opposing openings configured to receive an orthopedic rod, the connector assembly further having an upper threaded portion configured to receive a set screw and a bottom socket portion configured to cooperate with the spherical connector.

11. The orthopedic screw of claim 1, wherein the tip is cannulated so as to define a hole about the central axis of the main shaft.

12. The orthopedic screw of claim 1, wherein the leading edge of the distal-most thread extends in a plane non-parallel to the central axis of the main shaft.

* * * * *